US012589035B2

(12) United States Patent
      Bright

(10) Patent No.: US 12,589,035 B2
(45) Date of Patent: Mar. 31, 2026

(54) **BANDAGE SYSTEM FOR DETECTION OF *STAPHYLOCOCCUS ARUEUS* AND METHOD OF USE**

(71) Applicant: Emma J Bright, Liberty, MO (US)

(72) Inventor: Emma J Bright, Liberty, MO (US)

( * ) Notice: Subject to any disclaimer, the term of this patent is extended or adjusted under 35 U.S.C. 154(b) by 24 days.

(21) Appl. No.: 18/652,195

(22) Filed: May 1, 2024

(65) Prior Publication Data

US 2024/0366431 A1    Nov. 7, 2024

Related U.S. Application Data

(60) Provisional application No. 63/463,095, filed on May 1, 2023.

(51) Int. Cl.
      *A61F 13/00*          (2024.01)
(52) U.S. Cl.
      CPC .............................. *A61F 13/00059* (2013.01)
(58) Field of Classification Search
      CPC ....... A61F 13/00–0293; A61B 10/0045; A61B 10/0064; A61B 5/42; A61B 5/4261–4272
      See application file for complete search history.

(56) References Cited

U.S. PATENT DOCUMENTS

| | | | | |
|---|---|---|---|---|
| 5,203,327 A | * | 4/1993 | Schoendorfer | ...... A61B 5/4266 600/362 |
| 5,438,984 A | * | 8/1995 | Schoendorfer | ........ A61B 5/418 600/584 |
| 2004/0044299 A1 | * | 3/2004 | Utsugi | ................ A61F 13/0246 602/58 |
| 2023/0233113 A1 | * | 7/2023 | Levinson | ........... G01N 35/1009 600/309 |

FOREIGN PATENT DOCUMENTS

WO          WO-0030694 A1 *  6/2000  ............. A61L 15/44

* cited by examiner

*Primary Examiner* — Michelle J Lee
(74) *Attorney, Agent, or Firm* — AVEK IP, LLC

(57)          ABSTRACT

A disposable adhesive bandage capable of identifying the presence of *Staphylococcus aureus* ("*S. aureus*") at a wound site. By utilizing elements of existing rapid tests, a standard adhesive bandage can be upgraded to detect *S. aureus* or a proprietary bandage could be manufactured containing the necessary components for such detection without detracting from the bandage's primary capabilities of protecting and covering a wound site. In another embodiment, the bandage pad is manufactured to perform the steps of the testing surfaces.

10 Claims, 4 Drawing Sheets

BANDAGE SYSTEM FOR DETECTION OF *STAPHYLOCOCCUS ARUEUS* AND METHOD OF USE

CROSS-REFERENCE TO RELATED APPLICATION

This application claims priority in U.S. Provisional Patent Application No. 63/463,095, Filed May 1, 2023, which is incorporated herein by reference.

BACKGROUND OF THE INVENTION

1. Field of the Invention

The present invention relates generally to a bandage system and method for use thereof, and more specifically to a bandage configured to provide rapid detection of *Staphylococcus aureus.*

2. Description of the Related Art

*Staphylococcus aureus* ("*S. aureus*") is a hazardous disease if it is not caught in time. Doctors identified over 119,000 people in the United States with an *S. aureus* infection in their bloodstream, and almost 20,000 citizens died due to this bacterium according to the CDC.

Several differences exist between *S. aureus* and other *Staphylococcus* variants or other bacteria. No one factor of *S. aureus* makes it different from all other bacteria worldwide. However, in routine laboratory practice, the production of coagulase from *S. aureus* is frequently used as the sole criterion to distinguish *S. aureus* from other staphylococci, and there is a coagulase test. *S. aureus* also produces several other products that can be tested, for instance, capsular polysaccharides, protein A, and a toxin. Not all, but some *S. aureus* strains have also been known to produce Panton-Valentine Leucocidin, toxic shock syndrome 1 toxin (TSST-1), or other toxins.

Studies indicate that one-billion people in the world, at any given time, could give someone else a deadly infection or get a deadly disease themself. *S. aureus* is relatively harmless on healthy skin. If *S. aureus* is allowed to enter the bloodstream or the internal tissue, it becomes a health risk by way of infection. The way that *S. aureus* enters the bloodstream is most often when a wound is not properly treated, and the surrounding bacteria (in this case *S. aureus*) can invade the injured.

There are currently no tests for rapid identification of *S. aureus* that are easily accessible to the general public, it is evident that something had to happen to change the process. *S. aureus* is one of the most common bacterial infections that lead to complications such as bloodstream infections, pneumonia, or bone and joint infections. One such system for detecting *S. aureus* is the Pastorex Staph Plus system provided by Bio-Rad Laboratories, Inc. of Hercules, CA. When using Bio-Rad Pastorex Staph Plus, the *S. aureus* must be grown in a petri dish from the infected wound. What is needed is a way to quickly and easily detect *S. aureus* by end users outside of a lab or hospital environment.

Heretofore there has not been available a system or method for a bandage with the advantages and features of the present invention.

BRIEF SUMMARY OF THE INVENTION

The present invention generally provides a disposable adhesive bandage capable of identifying the presence of

*Staphylococcus aureus* ("*S. aureus*") at a wound site. By utilizing elements of existing rapid tests, a standard adhesive bandage can be upgraded to detect *S. aureus* or a proprietary bandage could be manufactured containing the necessary components for such detection without detracting from the bandage's primary capabilities of protecting and covering a wound site.

In a first embodiment, a standard bandage having a pair of adhesive wings bounding a central bandage pad forms the basis of the invention. A latex test testing strip and a negative control testing strip are placed onto or within the central bandage pad. A mesh top layer may be used to secure the test strips in place. Latex test drops and negative control drops may be required to activate the test strips which alert the user if an *S. aureus* infection is detected once placed about the wound site without falsely identifying other *Staphylococcus* or other infection types, including *Staphylococcus epidermidis.*

The test strips associated with Pastorex Staph Plus system provided by Bio-Rad Laboratories, Inc. of Hercules, CA shows clumping on the test strip when used with *S. aureus* coming into contact with the strip. In an alternative embodiment, the entire padded central area of the bandage could function as the *S. aureus* test site, increasing size and removing the need for additional steps of construction.

BRIEF DESCRIPTION OF THE DRAWINGS

The drawings constitute a part of this specification and include exemplary embodiments of the present invention illustrating various objects and features thereof.

DETAILED DESCRIPTION OF THE PREFERRED EMBODIMENTS

I. Introduction and Environment

As required, detailed aspects of the present invention are disclosed herein, however, it is to be understood that the disclosed aspects are merely exemplary of the invention, which may be embodied in various forms. Therefore, specific structural and functional details disclosed herein are not to be interpreted as limiting, but merely as a basis for the claims and as a representative basis for teaching one skilled in the art how to variously employ the present invention in virtually any appropriately detailed structure.

Certain terminology will be used in the following description for convenience in reference only and will not be limiting. For example, up, down, front, back, right and left refer to the invention as orientated in the view being referred to. The words, "inwardly" and "outwardly" refer to directions toward and away from, respectively, the geometric center of the aspect being described and designated parts thereof. Forwardly and rearwardly are generally in reference to the direction of travel, if appropriate. Said terminology will include the words specifically mentioned, derivatives thereof and words of similar meaning.

II. Preferred Embodiment Bandage System 2

Figure 1:
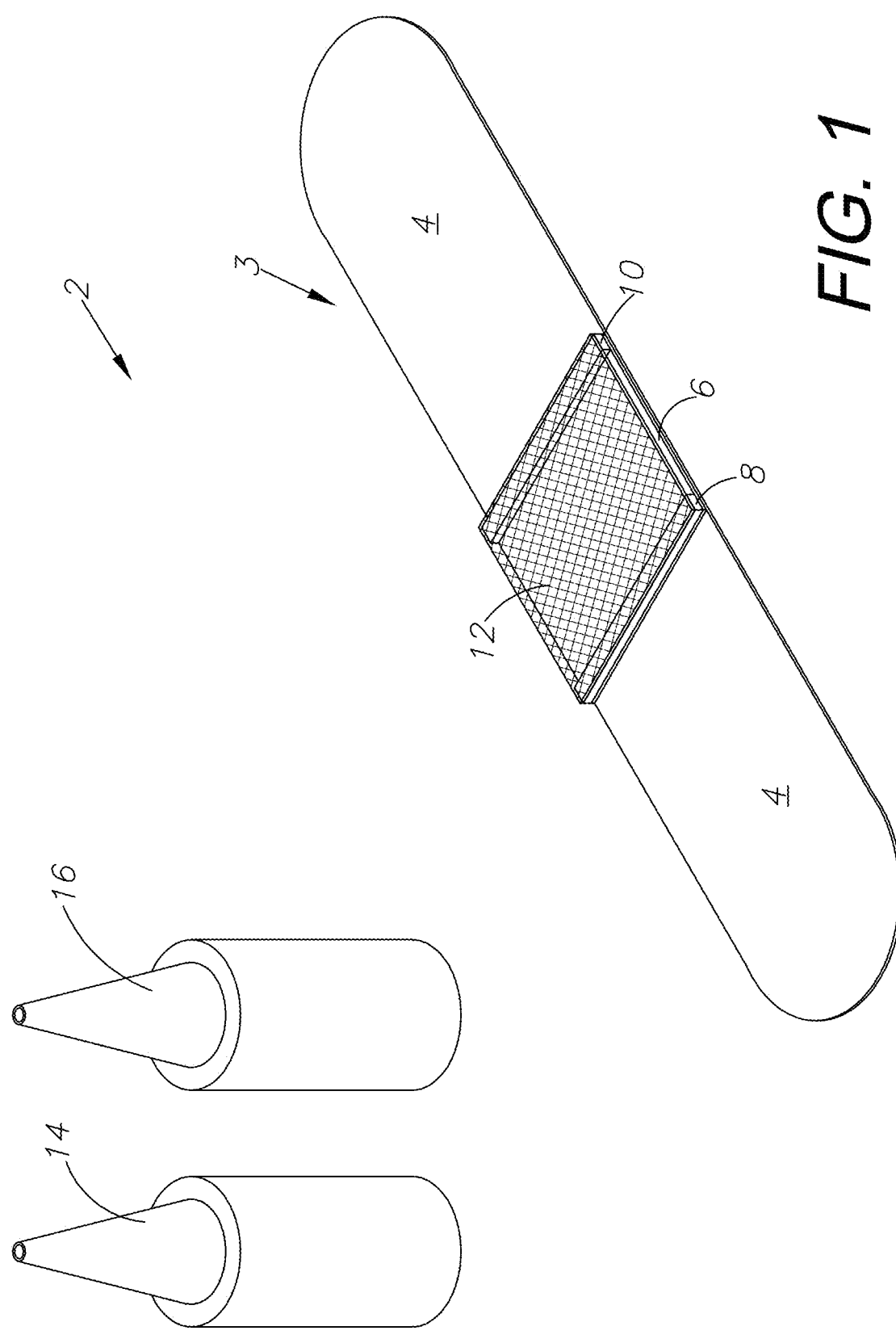
FIG. 1 is a three-dimensional isometric view of a preferred embodiment of the present invention shown in an assembled orientation.
Figure 2:
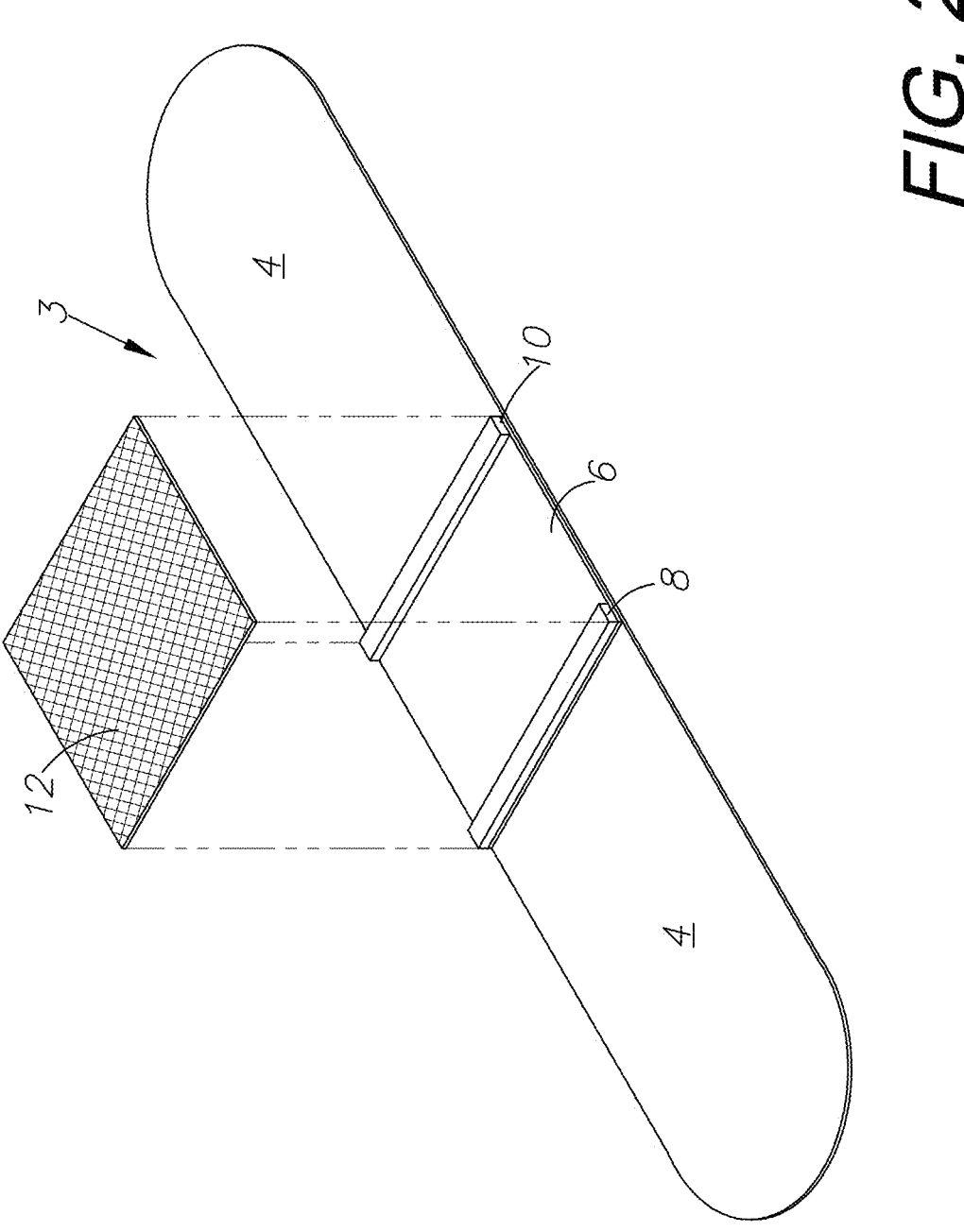
FIG. 2 is a partially-exploded three-dimensional isometric view thereof.
Figure 3:
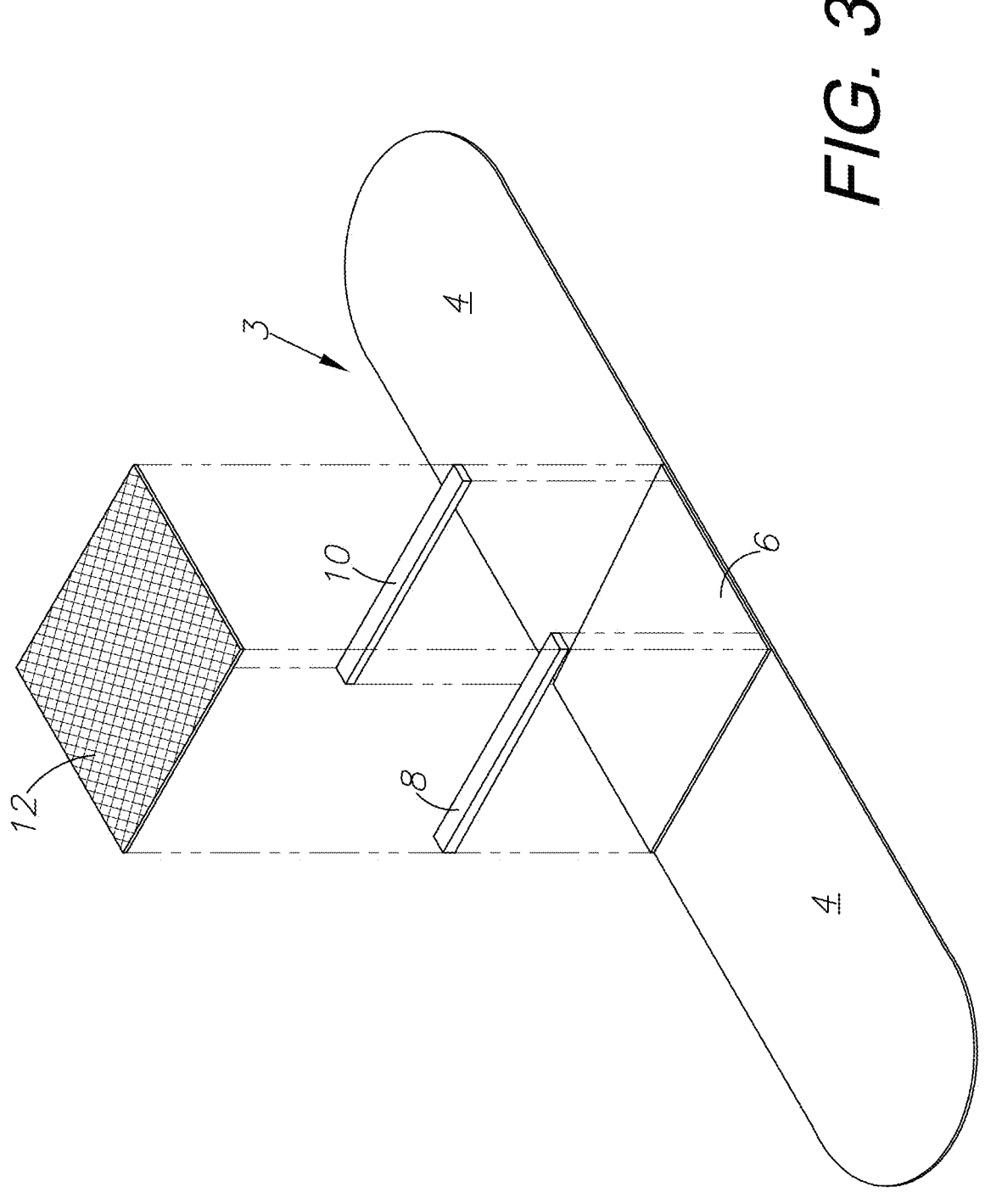
FIG. 3 is a fully-exploded three-dimensional isometric view thereof.

As shown in FIGS. 1-3, the present system teaches a bandage system 2 which is aimed at both securing a wound site while also testing that wound site to determine of any infections are present at the wound site. This system 2 could employ an existing bandage 3 which has a pair of adhesive-backed wings 4 and can include a central padded portion 6 typical of bandages, such as BAND-AID® adhesive bandages provided by Kenvue Inc. of Montgomery, NJ. This padded portion divides the bandage to have the pair of adhesive wings 4 on either side of the central padded portion 6.

A test surface 8 is included to detect whether *Staphylococcus aureus* ("*S. aureus*") is present at a wound site. Other infection types can also be targeted. This test surface 8 could be integrated into the central padded portion 6 directly, or it may be present in the form of a test strip 8 either affixed to or inserted into the central padded portion.

A negative control surface 10 could also be included alongside the test surface. This negative control surface would be able to then act as a control case to reduce false positives or false negatives.

A preferred embodiment could function without additional steps once the bandage is placed at the wound site. If *Staphylococcus aureus* is located at the wound site, the test surface 8 will indicate such by displaying results of a positive test to the user. This can be in the form of clumping appearing at the test site, or the test surface could be modified to present a color-coded or otherwise obvious determination of a positive or negative result.

An embodiment may require liquid drops 14, 16 to be placed between the test surface and the wound site. These liquid drops would activate with the test surface and the *S. aureus*, thereby causing the bandage to indicate that *S. aureus* is present at the wound site. The liquid drops may include a first bottle 14 of drops for the test case surface 8 and a second bottle 16 of drops for the control case surface 10.

Figure 4:
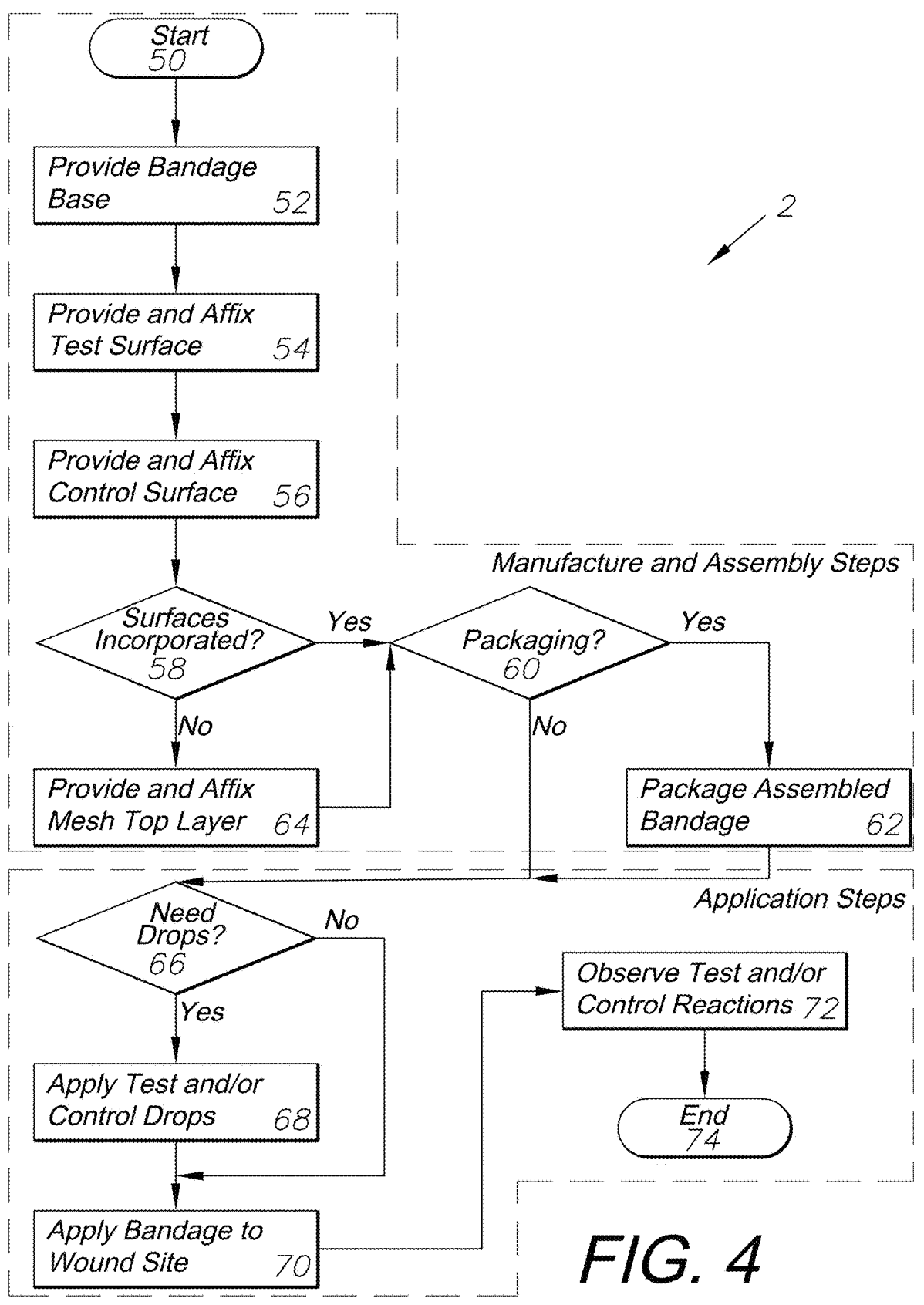
FIG. 4 is a flowchart diagramming the steps taken in practicing a method of the present invention.

FIG. 4 steps through the method of manufacturing and practicing the Bandage System 2. The Manufacture and Assembly Steps are shown on the upper half of the diagram, with the steps taken for Application Steps at a wound site shown at the bottom half. The process begins at the "start" step at 50.

At 52, a bandage base 3 is provided. This could be a preexisting bandage or it could be a new bandage assembled for the purposes of the present invention. The components of the bandage are shown in FIGS. 1-3.

The test surface is provided and applied to the bandage at 54, and similarly the control surface is provided and applied at 56. If those test and control surfaces are incorporated into the bandage pad 6 at 58, then no additional steps are needed to assemble the bandage system 2. Otherwise, a mesh top layer 12 may be applied at 64. This helps to secure the test and control surfaces 8, 10 to the bandage 3.

A determination may be made at 60 whether the bandage system 2 requires packaging for future use, or if the bandage is going to be used immediately without packaging. If packaging is required, the assembled bandage is packed into its packaging at 62. Otherwise, the bandage may proceed to the Application Steps phase.

A determination is made at the outset of the Application Steps phase of the process whether the liquid drops 14, 16 are required at 66. This will depend on the bandage assembly process, whether the test 8 and control 10 surfaces are incorporated into the bandage pad 6, and whether those test

8 and control 10 surfaces require drops for results to appear. If yes, the drops are placed at 68 at the wound site or on the bandage pad 6 directly. Otherwise, the bandage is simply applied to the wound site at 70. The bandage is then observed at 72 to determine if positive results are returned from the test surface 8, which is compared with the control surface 10 to determine false negative results. The process ends at 74.

It is possible that a fully manufactured, stand-alone adhesive bandage could provide the benefits of the present invention, and may produce the best and fastest results to end-users. In such an instance, the bandage pad 6 element may partially or fully incorporate the capabilities of the test surface 8 and/or the control surface 10 such that they would replace the need for testing strips to be used.

It is to be understood that while certain embodiments and/or aspects of the invention have been shown and described, the invention is not limited thereto and encompasses various other embodiments and aspects.

Having thus described the invention, what is claimed as new and desired to be secured by Letters Patent is:

1. A bandage system comprising:
a central pad having a first side edge, a second side edge, an upper edge, and a lower edge; and
a first flexible adhesive wing located along said first edge and a second flexible adhesive wing located along said second edge, said first and second flexible adhesive wings configured to secure said central pad about a wound site;
a test surface comprising a first strip located within said central pad, said test surface configured to detect an existence of an infection when said test surface is placed in contact with said infection;
said test surface further configured to visibly display positive results when said test surface is placed in contact with said wound site;
a negative control surface comprising a second strip located within said central pad, said negative control surface configured to detect for false-negative results; and
said negative control surface further configured to visibly display the false-negative results when said negative control surface is placed in contact with said wound site; and
wherein the test surface and negative control surface are on opposite longitudinal sides of the central pad such that the first and second strips extend from the upper edge to the lower edge to form the first and second side edges, respectively.

2. The system of claim 1, further comprising:
a first liquid substance contained within a first liquid container;
said first liquid substance configured to be deployed onto said test surface once placed onto said wound site; and
wherein said first liquid substance is configured to interact with said test surface to aid in a detection of the existence of said infection.

3. The system of claim 1, further comprising:
a second liquid substance contained within a second liquid container;
said second liquid substance configured to be deployed onto said negative control surface once placed onto said wound site; and
wherein said second liquid substance is configured to interact with said negative control surface to aid in a detection of said false-negative results of said infection.

4. The system of claim 1, wherein said infection comprises *Staphylococcus aureus* ("*S. aureus*").

5. The system of claim 1, further comprising:

said control surface configured to provide feedback resulting in a false-positive result from said test surface.

6. A method of manufacturing a bandage configured to detect an infection, the method comprising the steps:

providing a bandage having a pair of flexible wings comprising an adhesive face configured for adhering to a body surface, and said bandage further comprising a pad located between said pair of flexible wings, said pad configured for interfacing with a wound site within said body surface, wherein said pad comprises a first side edge, a second side edge, an upper edge, and a lower edge;

incorporating a test surface comprising a first strip within said pad, said test surface configured to detect a presence of an infection at said wound site;

incorporating a negative control surface comprising a second strip within said pad, said negative control surface configured to detect for false-negative results of the infection at said wound site;

producing a visual clumping response within said test surface as a result of detecting said infection at said wound site; and wherein the test surface and negative control surface are on opposite longitudinal sides of the pad such that the first and second strips extend from the upper edge to the lower edge to form the first and second side edges, respectively.

7. The method of claim 6, further comprising the steps:

providing a first liquid substance within a drop container;

placing at least one drop of said first liquid substance onto said test surface once placed over said wound site; and said at least one drop of said first liquid substance activating with said test surface, thereby causing the production of said visual clumping response.

8. The method of claim 7, further comprising the steps:

providing a second liquid substance within a drop container;

placing at least one drop of said second liquid substance onto said negative control surface once placed over said wound site; and said at least one drop of said second liquid substance activating with said negative control surface.

9. The method of claim 6, wherein said infection comprises *Staphylococcus aureus* ("*S. aureus*").

10. The method of claim 6, further comprising the steps:

said control surface configured to provide feedback resulting in a false-positive result from said test surface.

* * * * *